US00PP36261P2

(12) United States Plant Patent
Doguet et al.

(10) Patent No.: US PP36,261 P2
(45) Date of Patent: Nov. 19, 2024

(54) ZOYSIAGRASS PLANT NAMED 'BRG-2'

(50) Latin Name: ***Zoysia matrella* (L.) Merr.**
Varietal Denomination: BRG-2

(71) Applicants: David Doguet, Pleasanton, TX (US); Virginia Gail Lehman, Amarillo, TX (US)

(72) Inventors: David Doguet, Pleasanton, TX (US); Virginia Gail Lehman, Amarillo, TX (US)

( * ) Notice: Subject to any disclaimer, the term of this patent is extended or adjusted under 35 U.S.C. 154(b) by 0 days.

(21) Appl. No.: 18/831,019

(22) Filed: May 1, 2024

(51) Int. Cl.
*A01H 5/12* (2018.01)
*A01H 6/00* (2018.01)

(52) U.S. Cl.
USPC ..... Plt./390
CPC ..... *A01H 6/00* (2018.05)

(58) Field of Classification Search
USPC ..... Plt./390
CPC ..... A01H 5/12
See application file for complete search history.

*Primary Examiner* — Kent L Bell

(57) ABSTRACT

An asexually reproduced variety of perennial zoysiagrass with a unique combination of morphological characters including a very fine leaf texture, and increased leaf extension compared to 'Zeon' (U.S. Plant Pat. No. 13,166) when grown in hydroponic culture.

3 Drawing Sheets

Latin name of the genus and species of the plant claimed: The present invention relates to the genus and species *Zoysia matrella* (L.) Merr.

Variety denomination: 'BRG-2'.

BACKGROUND OF THE INVENTION

Field of Invention

The present invention relates to a new and distinct asexually reproduced variety of perennial zoysiagrass (*Zoysia matrella* (L.)) Merr.

BRIEF SUMMARY OF THE INVENTION

This invention relates to a new and distinct perennial zoysiagrass cultivar identified as 'BRG-2' zoysiagrass (herein referred to as 'BRG-2'). The inventors, David L. Doguet and Virginia G. Lehman, discovered 'BRG-2' under cultivated conditions near Poteet, TX in an area planted with 'Zeon' (U.S. Plant Pat. No. 13,166) zoysiagrass. 'BRG-2' was identified as a distinctly different vegetative patch or clonal plant differing from the surrounding plants in leaf texture. Tillers of 'BRG-2' were dug and transplanted to research plots for further evaluation and comparison to other plants. In research plots in Poteet, TX, in comparison to other zoysiagrass plants, 'BRG-2' showed the finest leaf texture with soft foliage when compared to other plants. The inventors asexually reproduced 'BRG-2' by taking vegetative cuttings of stolons and rhizomes, cutting the rhizomes and stolons into segments, each with a vegetative bud, and rooting them in potting media. 'BRG-2' zoysiagrass will be used as a turfgrass suitable for home lawns, sports fields, and golf courses.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Zoysingrass plant named 'BRG-2'.

BRIEF DESCRIPTIONS OF THE ILLUSTRATIONS

FIG. 1. 'BRG-2' zoysiagrass compared to a 'Primo' plant, unmown, from greenhouse pots.

FIG. 2. Inflorescence of 'BRG-2' zoysiagrass.

FIG. 3. Leaf texture of 'BRG-2' compared to 'Primo', unmown, from greenhouse pots.

COMPLETE BOTANICAL DESCRIPTION OF THE VARIETY

'BRG-2' was characterized in greenhouse and field conditions. 'BRG-2' is a unique variety of zoysiagrass (*Zoysia matrella* (L.)) Merr. that was discovered under cultivated conditions in a planting of 'Zeon' zoysiagrass. The inventors, David L. Doguet and Virginia G. Lehman, discovered 'BRG-2' near Poteet, TX in 2015. In 2015, vegetative rooted tillers of 'BRG-2' were collected from a vegetative plant or clone in a 'Zeon' (U.S. Plant Pat. No. 13,166) sod field that was under mowing. The tillers were placed in research plots with other plants for observation and increase. 'BRG-2' was identified as a distinctly different vegetative patch or clonal plant differing from variety 'Zeon' and other surrounding plants by having fine leaf texture. The plants were located in USDA Plant Hardiness Zone 8b. The inventors asexually reproduced 'BRG-2' in both Poteet, TX and Amarillo, TX by taking vegetative cuttings of stolons and rhizomes, cutting the rhizomes and stolons into segments, each with a vegetative bud, and rooting them in potting media. Planting of the rooted material provided planting stock for studying performance and for comparison of morphological characters after propagation. 'BRG-2' has been propagated by rhizomes, stolons, tillers, and sod. Asexually reproduced plants of 'BRG-2' have remained stable and true to type through successive generations of propagation. In 2020, a vegetative increase from the clonal plot of 'BRG-2' was made to a field plot of 1000 square feet to become the breeder stock of 'BRG-2'.

'BRG-2' is a perennial zoysiagrass that spreads by both stolons and rhizomes. Characteristics of 'BRG-2' measured in 2023 and 2024 were taken from plants that were approximately 12 months in age. The greenhouse was located near Amarillo, TX, with a nighttime low temperature of 67 degrees F., and daytime high of 80 degrees F. The plants were grown with a minimum 14-hour day length, supplemented with photosynthetically active radiation equivalent to approximately 75% sunlight. The plants were fertilized with the equivalent of 1 pound of actual N per month, using a soluble fertilizer of 20-20-20 in two equal soluble applications per month.

When evaluated for 86 days in Amarillo, TX under greenhouse conditions in potting soil, 'BRG-2' had a mean maximum leaf extension of 6.7 cm versus 10.3 cm for 'Zeon (U.S. Plant Pat. No. 13,166) or 35% less (Table 1). In a separate trial with low oxygen hydroponic root culture instead of soil media, 'BRG-2' had a mean maximum leaf extension of 5.7 cm versus 6.8 cm for 'Zeon' (Table 2). When grown under low-oxygen hydroponic culture versus growth under soil rooting media, 'BRG-2' maintained 85% of leaf extension growth compared to 'M-85' (U.S. Plant Pat. No. 27,289) at 67%, 'LIFS' (U.S. Plant Pat. No. 35,643) at 76%, and 'Zeon' (U.S. Plant Pat. No. 13,166) at 66%. Growth under low oxygen soil (hydroponic) conditions may suggest improved performance in turfgrass use where hypoxic soils exist. In field trials in Poteet, TX prior to a killing freeze below 28 degrees F. on 10 Jan. 2024, 'BRG-2' showed color retention under short daylengths associated with November to December 2023 calendar dates not different from 'Lazer' (U.S. Plant Pat. No. 32,805) (Table 3). After a freeze below 28 degrees F. on 10 Jan. 2024, 'BRG-2' performed similar to 'Lazer' in green color loss. In non-replicated trials during 2023, 'BRG-2' showed a ball speed roll of 9.8 feet with 'M-85' showing a speed of 8.2, slower than 'BRG-2'. In replicated trials in Soperton, GA during 2021, 'BRG-2' showed slightly less spread than 'M-85', with a rating of 6.7 (rated 1-9, 9=most spread), and 'M-85' rating a 7.0 (Table 4).

'BRG-2' has an absence of leaf hairs versus 'Palisades' (U.S. Plant Pat. No. 11,515), 'Zorro' (U.S. Plant Pat. No. 14,130), 'Crowne' (U.S. Plant Pat. No. 11,570), and 'Cavalier' (U.S. Plant Pat. No. 10,778) which each have many leaf surface hairs (Table 5). 'BRG-2' has shown a desirable very fine leaf texture under mowing. In observations, 'BRG-2'showed an internode length of 1.0 cm between the $3^{rd}$ and $4^{th}$ youngest leaf. 'BRG-2' has shown little tendency to form tillers in thatch that tend towards puffiness in canopy growth in cultivars such as 'Emerald' (unpatented) that subsequently require dethatching maintenance. 'BRG-2' has a leaf blade color from R.H.S. Colour Chart of 137B green, with 'Zeon' showing 137B green in greenhouse trials.

'BRG-2' has not shown susceptibility to the zoysiagrass mite when tested at Poteet, TX, where susceptible varieties have shown the coachwhip leaf symptoms of the mite. In plantings in Poteet, TX, 'BRG-2' showed mild susceptibility to warm season brown patch (*Rhizoctonia solani*). 'BRG-2' has shown good turfgrass performance and temperature adaptation when tested at Soperton, GA, USDA hardiness zone 8b and at Poteet, TX, USDA hardiness zone 9a. This would suggest adaptation as far north as the southern edge of Atlanta, GA, USDA hardiness zone 8a, that would extend the area of adaptation for 'BRG-2' in a line from central Georgia across central Alabama, extending through central Texas in an East/West line and on a North/South line from Norfolk, VA, south through Mexico. 'BRG-2' will be limited only by winter survival in colder regions. 'BRG-2' is similar to most fine textured zoysiagrasses in water use demands as shown in test situations near Poteet, TX, and will be limited by adequate precipitation in drier to arid regions. 'BRG-2' is adapted from sandy to heavier loam soil textures and from slightly acid to slightly alkaline soil pH.

TABLE 1

Canopy leaf extension at tip of youngest leaves on unmown tillers, measured with plants in potting soil media grown under greenhouse conditions in Amarillo, TX, 2023.

| | Leaf Extension Growth (canopy height) | | | |
|---|---|---|---|---|
| Variety | 14 days -cm- | 28 days -cm- | 57 days -cm- | Overall Mean, 86 days -cm- |
| 'BRG-2' | 2.6 | 5.1 | 10.9 | 6.7 |
| 'M-85' | 2.6 | 7.1 | 11.3 | 8.6 |
| 'L1FS' | 2.7 | 5.2 | 5.7 | 8.5 |
| 'Zeon' | 6.3 | 10.8 | 11.4 | 10.3 |

TABLE 2

Canopy leaf extension at tip of youngest leaves on unmown tillers, measured with plants in hydroponics, grown under greenhouse conditions in Amarillo, TX, 2023.

| | Leaf Extension Growth (canopy height) | | | |
|---|---|---|---|---|
| Variety | 14 days -cm- | 28 days -cm- | 57 days -cm- | Overall Mean, 86 days -cm- |
| 'BRG-2' | 3.0 | 3.9 | 9.6 | 5.7 |
| 'M-85' | 1.6 | 4.0 | 8.3 | 5.8 |
| 'L1FS' | 2.1 | 3.3 | 4.3 | 6.5 |
| 'Zeon' | 5.6 | 5.8 | 7.3 | 6.8 |

TABLE 3

Color retention rating (Rated 1-9, 9 = most green active growth) before and after low temperature exposure, Poteet, TX, 2024, in mowed turf plots.

| | Green color | |
|---|---|---|
| Variety | Before exposure | After exposure |
| 'BRG-2' | 7.0 | 4.0 |
| 'M-85' | 7.3 | 7.0 |
| 'Lazer'[&] | 7.0 | 4.0 |
| Lsd (p = 0.05) | 0.57 | 1.28 |

[&]'Lazer' is 'DALZ 1308', U.S. Plant Pat. No. 32,805

TABLE 4

Characteristics of zoysiagrass from a trial planted near Soperton, GA in 2020 and evaluated in 2021. Characteristics rated on a scale of 1-9 with 9 = best color, greatest spread, or least seedheads. Texture rated where VF = very fine and F = fine.

| Name | Leaf texture | Color | Spread | Seedhead presence |
|---|---|---|---|---|
| | | Year 2021 | | |
| 'BRG-2' | Vf | 7.3 | 6.7 | 9.0 |
| 'Lazer'& | Vf | 7.3 | 5.7 | 9.0 |
| 'M-85' | F | 6.3 | 7.0 | 9.0 |
| 'Trinity'& | F | 7.0 | 7.0 | 9.0 |
| Lsd, p = 0.05 | | 1.47 | 0.79 | 0.54 |

&'Trinity' is 'L1F', U.S. Plant Pat. No. 25,203
'Lazer' is 'DALZ 1308', U.S. Plant Pat. No. 32,805

TABLE 5

Adaxial leaf hair presence or absence of selected zoysiagrass cultivars, measured under greenhouse conditions in Amarillo, TX, 2022-23.

| Variety | Leaf hair, adaxial Presence/ Number |
|---|---|
| 'BRG-2' | Absent |
| 'L1FS'& | Sparse to Absent |
| 'L1F'& | Absent |
| 'Palisades'& | Many |
| 'Zorro'& | Many |
| 'Diamond'& | Absent |
| 'Royal'& | Absent |
| 'Crowne'& | Many |
| 'Cavalier'& | Many |

&'L1FS' is U.S. Plant Pat. No. 35,643; 'L1F' is U.S. Plant Pat. No. 25,203; 'Palisades' is U.S. Plant Pat. No. 11,515; 'Zorro' is U.S. Plant Pat. No. 14,130; 'Diamond' is U.S. Plant Pat. No. 10,636; 'Royal' is U.S. Plant Pat. No. 14,395; 'Crowne' is U.S. Plant Pat. No. 11,570; 'Cavalier' is U.S. Plant Pat. No. 10,778

COMPLETE BOTANICAL DESCRIPTION OF THE VARIETY

Color notations for floral and vegetative characters are based on The R.H.S. Colour Chart, 2001. Light quality, photoperiod, and general growth of the plants may affect color notations.

Origin: 'BRG-2' is a cultivar of a single clone discovered under cultivated conditions in a Poteet, TX sod field of 'Zeon' (U.S. Plant Pat. No. 13,166) zoysiagrass. 'BRG-2' was identified as a distinctly different vegetative patch or clonal plant by having a finer leaf texture than 'Zeon' and other surrounding plants.

Classification: *Zoysia matrella* (L.) Merr.

Mature plant height, including inflorescence: 'BRG-2': 9 cm.

Growth habit: 'BRG-2' is a perennial plant that spreads by stolons and rhizomes and produces a dense, low growing, very fine textured turfgrass. The inflorescence of 'BRG-2' is a terminal spike-like raceme, with spikelets on short pedicels.

Leaf blade: Rolled in the bud, flat surface.

Leaf blade pubescence: Absent to sparse on abaxial or adaxial leaf surface.

Leaf sheath pubescence: Absent except for long hairs at mouth of sheath 0.2-0.4 mm in length.

Leaf blade margin: 'BRG-2': entire without barbules.

Leaf blade veins: Prominent.

Leaf blade flexibility (softness): Soft.

Leaf blade color adaxial leaf surface: 'BRG-2': 137B.

Leaf blade color abaxial leaf surface: 'BRG-2': 137B.

Vegetative leaf, 2nd youngest vegetative leaf:

*Blade length range.*—'BRG-2': 3.4 cm to 7.2 cm.

*Blade width mean.*—'BRG-2': 0.6 mm to 0.9 mm.

Stolon leaf angle, third youngest leaf, measured on unmown, greenhouse 'BRG-2'grown plants: 25 to 30 degrees.

Stolon color: 164C greyed orange, 158A yellow white group.

Stolon density: Rated on a scale of 1-9 (9=highest density), 'BRG-2': 7; 'Meyer' (unpatented): 2.

Tendency to form puffy or clumpy turf: Rated on a scale of 1-9 (9=least puff), 'BRG-2': 8; 'Emerald': 2 (unpatented).

Inflorescence characters: 'BRG-2' has shown a sparse floral production unless under environmental stresses such as low water availability.

*Culm total length, including floral area to node below flag leaf.*—9 mm to 1.6 cm. Length of stem of inflorescence: 0.5 cm. Floral area length: 6.0 mm.

*Culm width, stem thickness, base of floral area.*—0.4 mm.

*Spikelet length.*—2.0 mm to 3 mm.

*Spikelet width.*—0.6 mm to 0.7 mm.

*Stigma.*—155A White.

*Anther length.*—1 mm.

*Node thickness, node below flag leaf.*—0.3 mm to 0.4 mm.

*Pedicel length.*—2.0 mm.

*Flag leaf length.*—1.6 mm.

*Flag leaf width.*—0.7 mm.

*Inflorescence emergence.*—'BRG-2' has very sparse flowering in Poteet, TX from late April through October.

Turf quality (rated 1-9, 9 best), mowed at fairway height: 'BRG-2': 8; 'Meyer': 3.

Turf color rating (rated 1-9, 9 best) 'BRG-2': 7.3; 'Prizm' is 'M60' U.S. Plant Pat. No. 29,143.

I claim:

1. A new and distinct variety of zoysiagrass plant, substantially as described and illustrated herein, characterized particularly by a unique combination of morphological characters.

* * * * *

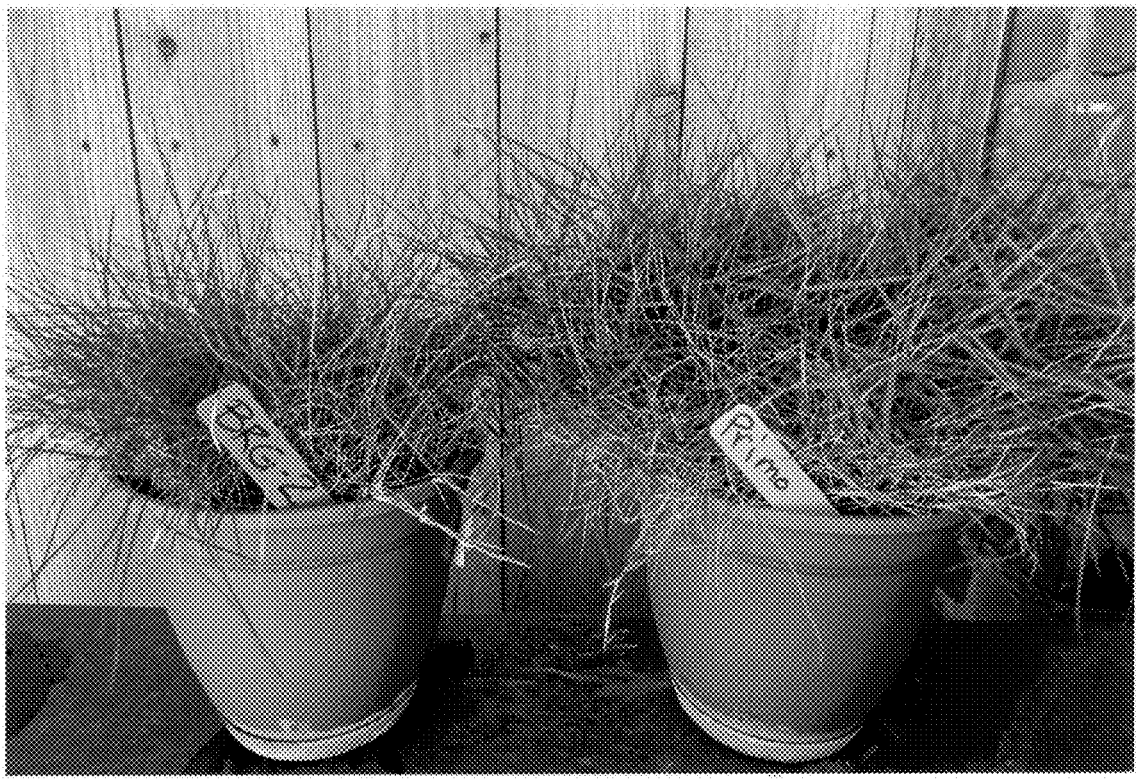
Figure 1. 'BRG-2' zoysiagrass compared to a 'Primo' plant, unmown, from greenhouse pots.

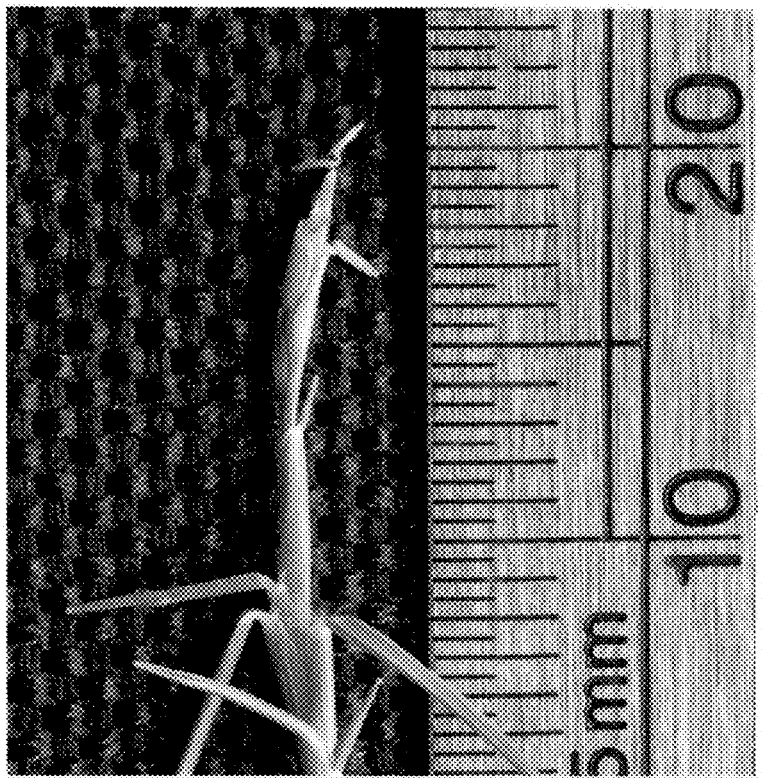
Figure 2. Inflorescence of 'BRG-2 zoysiagrass.

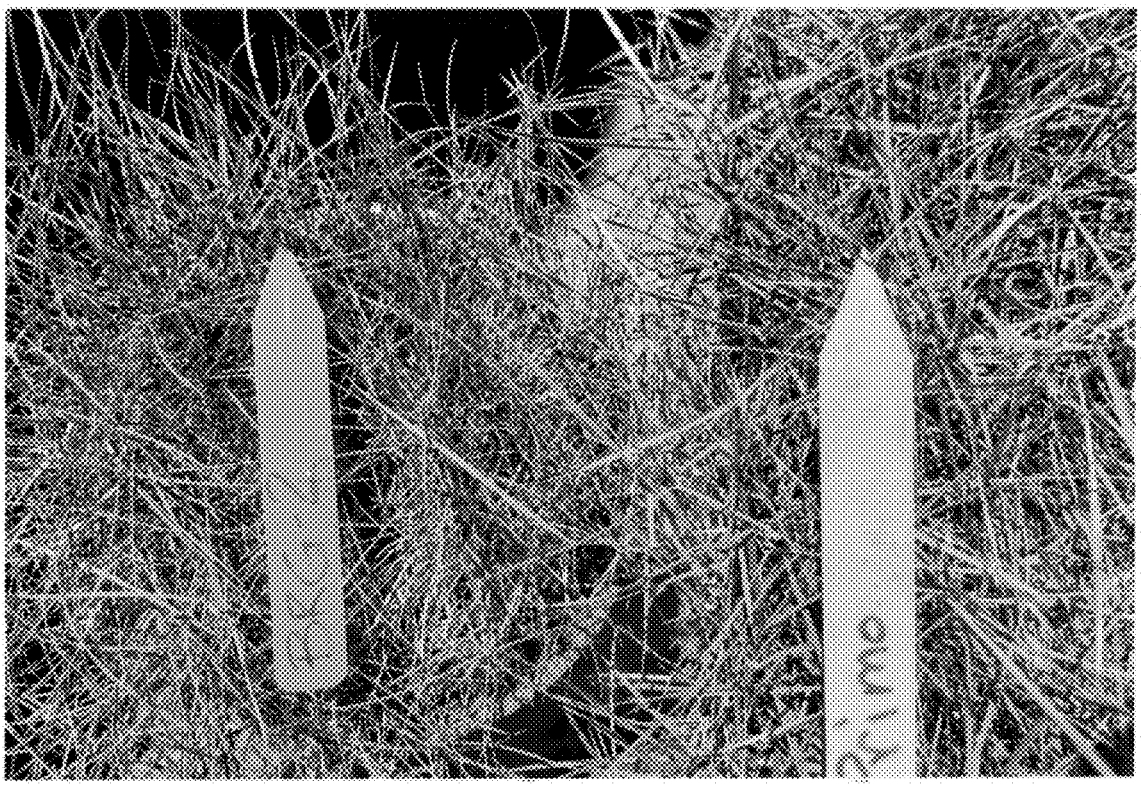
Figure 3. Leaf texture of 'BRG-2' compared to 'Primo', unmown, from greenhouse pots.